US00PP25086P2

(12) United States Plant Patent
Fitzgerald

(10) Patent No.: US PP25,086 P2
(45) Date of Patent: Nov. 18, 2014

(54) ***CAREX* PLANT NAMED 'EVERDI'**

(50) Latin Name: *Carex oshimensis*
Varietal Denomination: Everdi

(71) Applicant: Pat Fitzgerald, Old Town (IE)

(72) Inventor: Pat Fitzgerald, Old Town (IE)

( * ) Notice: Subject to any disclaimer, the term of this patent is extended or adjusted under 35 U.S.C. 154(b) by 35 days.

(21) Appl. No.: 13/815,449

(22) Filed: Mar. 4, 2013

(51) Int. Cl.
*A01H 5/00* (2006.01)

(52) U.S. Cl.
USPC ..... Plt./384

(58) Field of Classification Search
CPC ..... A01H 5/12; A01H 5/00; A01H 5/02; A01H 5/04; A01H 5/10
USPC ..... Plt./384
See application file for complete search history.

*Primary Examiner* — June Hwu
(74) *Attorney, Agent, or Firm* — Penny J. Aguirre

(57) ABSTRACT

A new cultivar of *Carex oshimensis*, 'Everdi', characterized its dwarf plant habit and its dark green foliage.

2 Drawing Sheets

Botanical classification: *Carex oshimensis.*
Varietal denomination: 'Everdi'.

BACKGROUND OF THE INVENTION

The present invention relates to a new and distinct cultivar of *Carex oshimensis* and will be referred to hereafter by its cultivar name, 'Everdi'. 'Everdi' is a new cultivar of perennial ornamental grass grown for container and landscape use, primarily in shaded exposures.

The new cultivar, 'Everdi' arose as a naturally occurring chimeral mutation of *Carex oshimensis* 'Evergold' (not patented). The Inventor discovered 'Everdi' in August of 2008 in a container at his nursery in Oldtown, Stoneyford, Co. Kilkenny, Republic of Ireland.

Asexual propagation of the new cultivar was first accomplished by rhizome division in Oldtown, Stoneyford, Co. Kilkenny, Republic of Ireland in May of 2009 by the Inventor. Asexual propagation of the new cultivar by rhizome division and basal cuttings has determined that the characteristics are stable and are reproduced true to type in successive, generations.

SUMMARY OF THE INVENTION

The following traits have been repeatedly observed and represent the characteristics of the new cultivar. These attributes in combination distinguish 'Everdi' as a distinct cultivar of *Carex*.

1. 'Everdi' exhibits a dwarf plant habit.
2. 'Everdi' exhibits dark green foliage.

'Evergold', the parent plant of 'Everdi' differs from 'Everdi' in having a taller plant habit and in having foliage that is variegated with creamy-yellow centers and green margins. 'Everdi' can be most closely compared to the cultivar 'Everillo' (U.S. Plant Pat. No. 21,002), which differs from 'Everdi' in having foliage that is solid yellow in color. Unnamed plants of the species *Carex oshimensis* have green foliage, however the plants are taller in plant height and have lighter green foliage. All other cultivars of *Carex oshimensis* known to the Inventor that exhibit foliage that is variegated.

BRIEF DESCRIPTION OF THE DRAWING

The accompanying colored photographs illustrate the overall appearance and distinct characteristics of six month-old plants the new *Carex* as grown in 17-cm containers outdoors in Oldtown, Stoneyford, C. Kilkenny, Ireland.

The photograph in FIG. 1 illustrates the dwarf plant habit and appearance of 'Everdi' in bloom.

Figure 1:
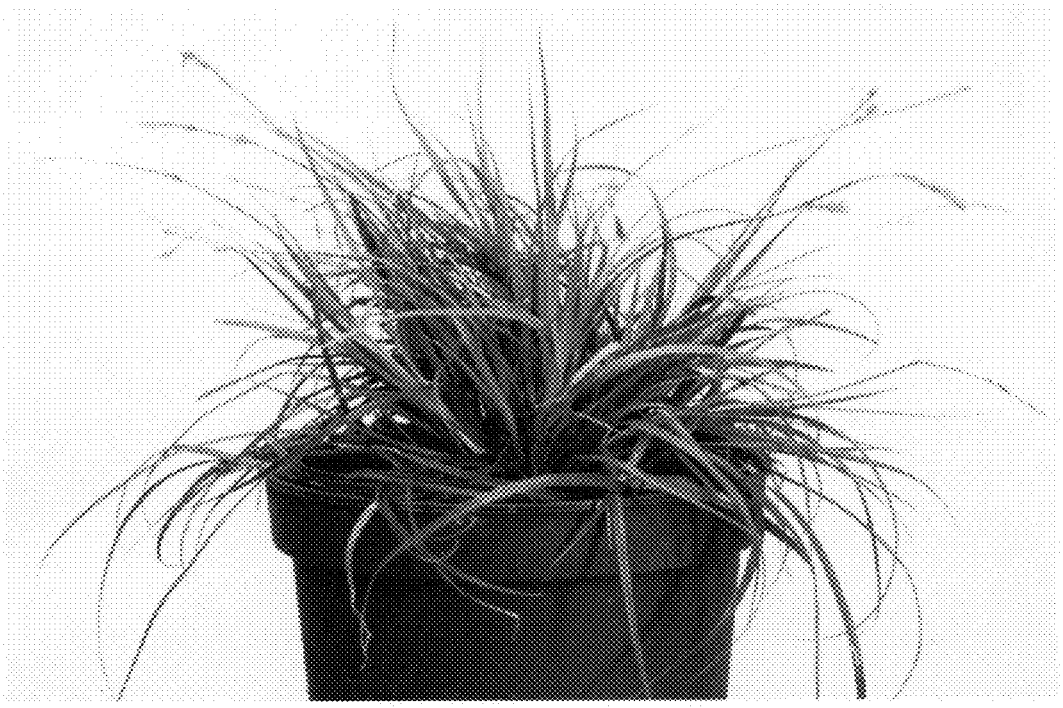
Figure 2:
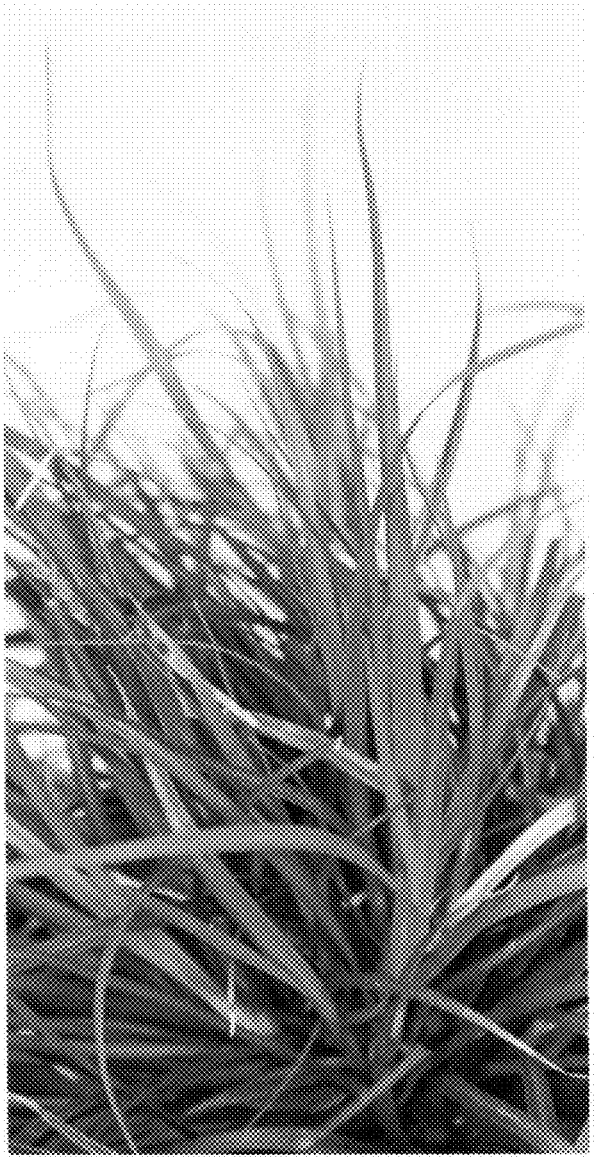

The photograph in FIG. 2 provides a close-up view of the foliage of 'Everdi'.

The colors in the photograph may differ slightly from the color values cited in the detailed botanical description, which accurately describe the colors of the new *Carex*.

DETAILED BOTANICAL DESCRIPTION

The following is a detailed description of six month-old plants as grown outdoors in a nursery in 17-cm containers in Co. Kilkenny, Republic of Ireland. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Inflorescences emerge in January and continue into summer in the Republic of Ireland.

*Plant habit.*—Herbaceous perennial, flattened globular with arching leaves and inflorescences.

*Growth habit.*—Broad, spreading.

*Height and spread.*—Reaches about 16.6 cm in height, spreads to about 31 cm in diameter.

*Hardiness.*—At least in U.S.D.A. Zones 6 to 9.

*Plant vigor.*—Moderate.

*Diseases and pests.*—Not more susceptible to pests and diseases than other *Carex* varieties.

*Root description.*—Short, stout rhizomes with dense, fibrous roots, roots moderately branched.

*Propagation.*—Rhizome division and basal cuttings.

*Branching.*—Average of 41 main shoots grow from the base, no lateral branches.

Foliage description:

*Leaf shape.*—Linear, strongly curved (arching).

*Leaf division.*—Simple.

*Leaf base.*—Sheathed to rhizome, triangular in shape.

*Leaf apex.*—Long acuminate.

*Leaf aspect.*—Leaves initially emerge upright, then cascade outward and finally arch downward until the terminal blades lay on the ground.

*Leaf venation.*—Parallel.

*Leaf margins.*—Entire and slightly sharp when rubbed downwards due to very small teeth too small to be seen or measured.

*Leaf size.*—Matures to an average of 16.8 cm in length and 4 mm in width.

*Leaf number.*—Average of 10 leaves per shoot.

*Leaf arrangement.*—Alternate.

*Leaf surface.*—Glossy and smooth.

*Leaf color.*—Young upper surface; 143A to 144A, young lower surface; 144A, mature upper surface; N137A to N137B, mature lower surface; N137A.

*Durability to stresses.*—High.

*Petiole.*—No petioles, leaves sheathing; average width 0.3 cm and 177B to 177C in color.

Flower description:

*General description.*—Terminal racemes, male and female flowers on separate spikelets.

*Inflorescence size.*—Average of 5.1 cm in height and 1.3 cm in width.

*Flower quantity per inflorescence.*—Average of 30 male flowers placed in an average of 1 spikelet and an average of 24 female flowers placed in an average of 1 spikelet.

*Lastingness of inflorescence.*—Flowers last about 10 days.

*Flowering season.*—Continuous from late winter into summer.

*Response time to flower.*—Approximately 8 months.

*Rate of flower opening.*—After first initial flowers open in an inflorescence all flowers open within 3 weeks.

*Fragrance.*—None.

*Flower buds.*—Male flower: average of 1.4 cm in length and 3 mm in diameter, narrow oblong in shape and 199D in color, female flower: average of 0.5 cm in length and 3 mm in width, narrow obovate in shape and 144C to 145A in color.

*Spikelet shape.*—Sedge-like, narrowly ovate.

*Persistence of spikelets.*—Persistant.

*Floret (spikelet) size.*—Staminate florets; an average of 1 mm in diameter and 6 mm in length, pistillate florets; an average of 1 mm in diameter and 5 mm in length.

*Floret (spikelet) description.*—1 glume on inner side and 1 lemma on outer side, male flower: average of 1 glume and 1 lemma, glume and lemma surfaces smooth and dull, glume and lemma lanceolate in shape, glume and lemma entire margin, glume apex long, narrow and acute, lemma apex long and mucronate, glume and lemma 6 mm in length and 0.75 mm in width, glume and lemma color: upper and lower surface when opening; 161D, upper and lower surface when fully opened; 161D, female flower: (no glume), lemma; 1, smooth and dull surfaces, lanceolate in shape, entire margin, apex long and mucronate, average of 5 mm in length and 1 mm in width, color: upper and lower surface when opening; 150D, apex 161C, upper and lower surface when fully opened; 150D, apex161C.

*Peduncle.*—An average of 17.4 cm in length and 1 mm in diameter, held upright to 15° to upright, strong, 137C in color becoming 143B towards apex.

Reproductive organs:

*Gynoecium.*—Average of 1 pistil about 1 mm in length, stigma is fimbriate and 199A in color, style is about 0.5 mm in length and 144B in color, ovary is 144B in color.

*Androcoecium.*—Average of 3 stamens, basifixed, about 2 mm in length and 164B in color, pollen production very low and insufficient in quantity to be color coded.

*Fruits and seeds.*—Seed production has not been observed to date.

It is claimed:

1. A new and distinct cultivar of *Carex* plant named 'Everdi' as herein illustrated and described.

* * * * *